US012797127B2

(12) United States Patent
Katoh et al.

(10) Patent No.: US 12,797,127 B2
(45) Date of Patent: Nov. 17, 2026

(54) RECANALIZING OCCLUDED VESSELS USING RADIOFREQUENCY ENERGY

(71) Applicant: Asahi Medical Technologies, Inc., Pleasanton, CA (US)

(72) Inventors: Osamu Katoh, Nagoya (JP); Wayne Ogata, San Ramon, CA (US)

(73) Assignee: Asahi Medical Technologies, Inc., Pleasanton, CA (US)

( * ) Notice: Subject to any disclaimer, the term of this patent is extended or adjusted under 35 U.S.C. 154(b) by 0 days.

(21) Appl. No.: 19/185,910

(22) Filed: Apr. 22, 2025

(65) Prior Publication Data

US 2025/0248759 A1 Aug. 7, 2025

Related U.S. Application Data

(63) Continuation of application No. 16/674,857, filed on Nov. 5, 2019, now Pat. No. 12,285,205, which is a (Continued)

(51) Int. Cl.

*A61B 18/14* (2006.01)
*A61B 5/00* (2006.01)
(Continued)

(52) U.S. Cl.

CPC ........ *A61B 18/1492* (2013.01); *A61B 5/0059* (2013.01); *A61B 8/12* (2013.01); *A61B 18/18* (2013.01); *A61B 18/1815* (2013.01); *A61B 18/245* (2013.01); *A61B 90/37* (2016.02); *A61M 5/00* (2013.01); *A61M 13/003* (2013.01); *A61B 5/0066* (2013.01); *A61B 2018/00029* (2013.01); *A61B 2018/00285* (2013.01); *A61B 2018/00291* (2013.01); *A61B 2018/0041* (2013.01); *A61B 2018/00839* (2013.01); *A61B 2018/00982* (2013.01); *A61B 2018/1861* (2013.01); *A61B 18/24* (2013.01); *A61B 2090/378* (2016.02);
(Continued)

(58) Field of Classification Search

CPC ... A61B 18/1492; A61B 90/37; A61B 5/0059; A61B 8/12; A61B 18/18; A61B 18/1815; A61B 18/245; A61B 2090/378; A61B 2090/3782; A61B 5/0066; A61B 18/24; A61B 2018/00029; A61B 2018/00285; A61B 2018/00291; A61B 2018/0041; A61B 2018/00839; A61B 2018/00982; A61B 2018/1861; A61M 5/00; A61M 13/003; A61N 7/022

USPC .......................................................... 606/42

See application file for complete search history.

(56) References Cited

U.S. PATENT DOCUMENTS

2004/0122422 A1* 6/2004 Ein-Gal ............ A61B 17/3478 604/20
2004/0230212 A1* 11/2004 Wulfman ....... A61B 17/320758 606/167
2005/0182319 A1* 8/2005 Glossop .............. A61B 6/5247 600/424

* cited by examiner

*Primary Examiner* — Aaron F Roane
(74) *Attorney, Agent, or Firm* — Oliff PLC

(57) ABSTRACT

A method and systems for treating chronic total occlusions, particularly those that are difficult to treat, is disclosed. In this approach, recanalizing the CTO is achieved using a combined antegrade and retrograde approach. The proximal end of the occlusion is penetrated using an antegrade wire, using a traditional approach. Using collateral vessels, the distal end of the occlusion is crossed in a retrograde fashion. By appropriately maneuvering each member and applying radiofrequency energy between the proximal and distal ends of the occlusion, a continuous channel is created.

11 Claims, 18 Drawing Sheets

Related U.S. Application Data continuation of application No. 15/003,098, filed on Jan. 21, 2016, now Pat. No. 10,492,855, which is a continuation of application No. 13/639,092, filed as application No. PCT/US2011/031018 on Apr. 1, 2011, now Pat. No. 9,271,787, which is a continuation-in-part of application No. 12/680,500, filed on Aug. 3, 2010, now Pat. No. 8,911,435, and a continuation of application No. 12/753,844, filed as application No. PCT/US2008/077403 on Sep. 23, 2008, now Pat. No. 9,283,034.

(60) Provisional application No. 61/298,547, filed on Jan. 26, 2010, provisional application No. 60/975,473, filed on Sep. 26, 2007.

(51) Int. Cl.

| | |
|---|---|
| ***A61B 8/12*** | (2006.01) |
| ***A61B 18/18*** | (2006.01) |
| ***A61B 18/24*** | (2006.01) |
| ***A61B 90/00*** | (2016.01) |
| ***A61M 5/00*** | (2006.01) |
| ***A61M 13/00*** | (2006.01) |
| *A61B 18/00* | (2006.01) |
| *A61N 7/02* | (2006.01) |

(52) U.S. Cl.

CPC ....... *A61B 2090/3782* (2016.02); *A61N 7/022* (2013.01)

RECANALIZING OCCLUDED VESSELS USING RADIOFREQUENCY ENERGY

This application is a continuation of U.S. patent application Ser. No. 16/674,857, filed Nov. 5, 2019, which is a continuation of prior U.S. patent application Ser. No. 15/003,098, filed Jan. 21, 2016, which is a continuation of prior U.S. patent application Ser. No. 13/639,092, filed Jan. 18, 2013, which is a National Stage Application under 35 U.S.C. § 371 of PCT/US2011/31018, filed Apr. 1, 2011, which is a continuation of U.S. patent application Ser. No. 12/753,844, filed Apr. 2, 2010, which is a continuation-in-part of U.S. patent application Ser. No. 12/680,500, filed Aug. 3, 2010, which is a National Stage Application under 35 U.S.C. § 371 of PCT Application No. PCT/US2008/077403, filed Sep. 23, 2008, which claims the priority benefit of U.S. Provisional Patent Application Ser. No. 60/975,473, filed Sep. 26, 2007, each of which is hereby incorporated by reference in their entirety. U.S. application Ser. No. 12/753,844 also claims priority to U.S. Provisional Application Ser. No. 61/298,547, filed on Jan. 26, 2010, which is hereby incorporated by reference in its entirety.

TECHNICAL FIELD

This invention relates generally to dealing with occlusions of the lumen and more specifically to apparatus and methods for crossing severe or total chronic occlusions of lumens in the body using radiofrequency energy.

BACKGROUND

Chronic total occlusion (CTO) is the complete blockage of a vessel and may have serious consequences if not treated in a timely fashion. The blockage could be due to atheromatous plaque or old thrombus. One of the common procedures for treating CTOs of the coronary arteries is percutaneous transluminal coronary angioplasty (PTCA). During a PTCA procedure, a small incision is typically made in the groin. A guiding catheter over a guidewire is introduced into the femoral artery and advanced to the occlusion. At times, with gentle maneuvering, the guidewire is able to cross the occlusion. A balloon-tipped angioplasty catheter is then advanced over the guidewire to the occlusion. The balloon is inflated, separating or fracturing the atheroma. Often times, a stent is subsequently or simultaneously deployed. Some of the common steps involved in the PTCA procedure for CTOs are the simultaneous injection of a contrast agent in the contra-lateral vessel, securing backup force or stabilization for a guidewire (which could invoke additional personnel to handle the catheter), puncturing the plaque, drilling or rotating the guidewire to push it through the dense plaque, etc. Because of the stiff resistance sometimes offered by dense plaque, one could be forced to use stiff wires. Occasionally, the wires could puncture the vessel wall calling for remedial measures.

The most common percutaneous coronary intervention (PCI) failure mode for CTOs is inability to successfully pass a guidewire across the lesion into the true lumen of the distal vessel. To date, there is no consensus on how best to treat CTO after attempts with conventional guidewires have failed. Different strategies for CTOs have been developed including the side branch technique, the parallel wire technique, and the IVUS guided technique. Mechanical and energy based devices have also been proposed for passing guidewires through hard calcified occlusions, such as mechanical cutting or oscillation and laser or ultrasound or radiofrequency (RF) energy ablation. Each of these devices works by strictly utilizing an antegrade approach and locally applying energy (typically in the form of heat) at the tip of the guidewire or catheter device in order to create a channel and hopefully enter the distal true lumen.

RF energy is widely used to coagulate, cut or ablate tissue. In both modalities, monopolar and bipolar, conductive electrodes contact the tissue to be treated. In the monopolar mode, the active electrode is placed in contact with the tissue to be treated and a return electrode with a large surface area is located on the patient at a distance from the active electrode. In the bipolar mode, the active and return electrodes are in close proximity to each other bracketing the tissue to be treated. Sometimes an array of electrodes is used to provide better control over the depth of penetration of the RF field and hence control over the temperatures to which the tissue is heated. There are many disadvantages with each mode. For example, in the monopolar arrangement, because of the large physical separation between the electrodes there are frequent reports of local burning at the electrode sites. This would clearly be undesirable where one of the electrodes will be inside a blood vessel. The other serious issue is the likelihood of forming blood clots. The tissue that is in contact with the electrodes can be coagulated or ablated. In the case of the electrodes being present inside a blood vessel, the formation of dangerous blood clots would obviously be undesirable.

In an attempt to overcome the issues described above, various device and electrode configurations are described in the following patents. U.S. Pat. Nos. 5,366,443 and 5,419,767 describe the use of RF electrodes on a catheter to cross a lesion. These patents describe a bipolar electrode assembly at the distal tip of a catheter that is in contact with the occlusion, and patentees state that application of RF energy ablates the occlusion and renders the occlusion susceptible for the guidewire to penetrate. This method has the draw back that careful tracking of the occlusion and the ablation process is necessary to avoid trauma to the vessel walls or healthy tissue, since the possibility of short-circuiting of current through healthy tissue instead of the occlusion is high. U.S. Pat. No. 5,419,767 overcomes this limitation to a certain extent through the use of a multiple electrode array. However, this device requires a channel to be pre-created through the occlusion so that the device can be passed through a guidewire traversing this channel, which is not always easy.

U.S. Pat. No. 5,514,128 to Hilsman et al. describes a laser catheter device that enables ablation of an occlusion in the vasculature. This system has similar drawbacks to the ones described above-need for a guidance system, potential for healthy tissue to be ablated, complexity (and hence cost) of the device, etc.

One major problem with the existing devices is the potential for the ablation energy to damage the walls of the vasculature, in the absence of a mechanism to track the orientation and position of the energy delivery member. Several devices exist in the prior art that address the issue of tracking and steering of the energy delivery element. U.S. Pat. No. 6,911,026 to Hall et al. describes a magnetic steering and guidance system to direct an ablation device that delivers RF energy at the tip in a unipolar configuration where the return electrode is placed externally in contact with the body or in a bipolar configuration where the return electrode is a ring surrounding the central wire electrode.

U.S. Pat. No. 6,416,523 to Lafontaine discusses a mechanical cutting device where the guidance is provided by measuring impedance of the tissue in contact. The guidance system senses the difference in impedance between the stenotic tissue and the vessel wall and directs the cutting element to the occlusion.

However, none of these alternate strategies have provided satisfactory results for the most challenging of the CTOs. In case of hard calcified occlusions, the revascularization procedure can be tedious and time consuming. Therefore, there is a need for improved methods of ablating or disrupting the occlusive material that are safe, efficacious and fast. It would be beneficial to have alternate techniques and devices that would recanalize a CTO without the shortcomings of the current techniques.

CTOs that are hard to recanalize, either because of the tortuous anatomy of the diseased vessel, or because the proximal end of the stenosis is too hard for the guide wire to penetrate, or other characteristics of the CTO that would make the standard procedure vulnerable to failure would benefit from newer approaches to recanalize CTOs. Recently a combined antegrade-retrograde approach has been proposed for recanalizing chronic occlusions (U.S. application Ser. No. 11/706,041). The method disclosed in the co-pending application would benefit from the use of energy for crossing CTOs.

SUMMARY

Various methods and devices are provided to overcome some of the commonly encountered problems in treating chronic total occlusions. One aspect of this invention is to provide a method and systems for successfully recanalizing an occluded vessel by advancing, in combination, guidewires in an antegrade and retrograde fashion to the occlusion and applying RF energy between the proximal and distal ends of the occlusion. The RF energy application across the occlusion is accomplished using a bipolar arrangement, where one electrode is located on the antegrade guidewire and the other electrode that makes up the bipolar arrangement is located on the retrograde guidewire. In one aspect, the present invention discloses a method of recanalizing an occluded vessel comprising advancing in an antegrade fashion a first longitudinal member through a proximal end of an occlusion, advancing in a retrograde fashion a second longitudinal member through a distal end of the occlusion, applying RF energy between the distal ends of the antegrade and retrograde guidewires, ablating the tissue locally, and creating a channel through which a guidewire could be advanced. In another embodiment, the retrograde guidewire could have a deployable capture mechanism at its distal end and upon deployment could snare the antegrade guidewire.

In another aspect, this invention relates to a catheter assembly for recanalizing an occluded vessel comprising an antegrade longitudinal member with a distal end containing an RF electrode and a retrograde longitudinal member with a distal end containing a second RF electrode; and the proximal end of the catheter assembly connected to an RF generator. Additionally, a temperature measuring element could be disposed on the distal ends of the antegrade or retrograde longitudinal member. The RF generator could also be programmed to treat the tissue for a pre-set time or until a set condition has been reached. One such condition could be till the occlusion has reached a pre-determined temperature. Another condition could be the impedance of the occlusion.

In another aspect, the invention is a kit for recanalizing occluded vessels comprising one or more of the following: an antegrade guidewire, a retrograde guidewire, a dilating device, a capture device and an injection catheter, wherein at least one of these devices contains at least one electrode. Additionally, the proximal ends of this device are configured to be coupled with an RF generator.

In another aspect, a system for recanalizing occluded vessels may comprise two antegrade longitudinal members, wherein at least one longitudinal member may comprise a distal end that is capable of being redirected. The redirected distal end may substantially position in a retrograde fashion towards the occlusion. Alternatively, the redirected distal end may be substantially positioned towards the distal end of another longitudinal member. In another aspect, at least one longitudinal member may comprise an interior lumen configured to deliver a fluid to the occlusion.

In yet another aspect, the invention relates to a catheter positioning system with a balloon catheter comprising an inflatable balloon, a delivery catheter disposed within the balloon catheter, wherein upon inflation of the balloon, a position of the balloon catheter is substantially fixed, and wherein the delivery catheter is configured to advance through the balloon catheter without substantially altering the position of the balloon catheter.

Other aspects of the invention include methods corresponding to the devices and systems described above.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION

Figure 1:
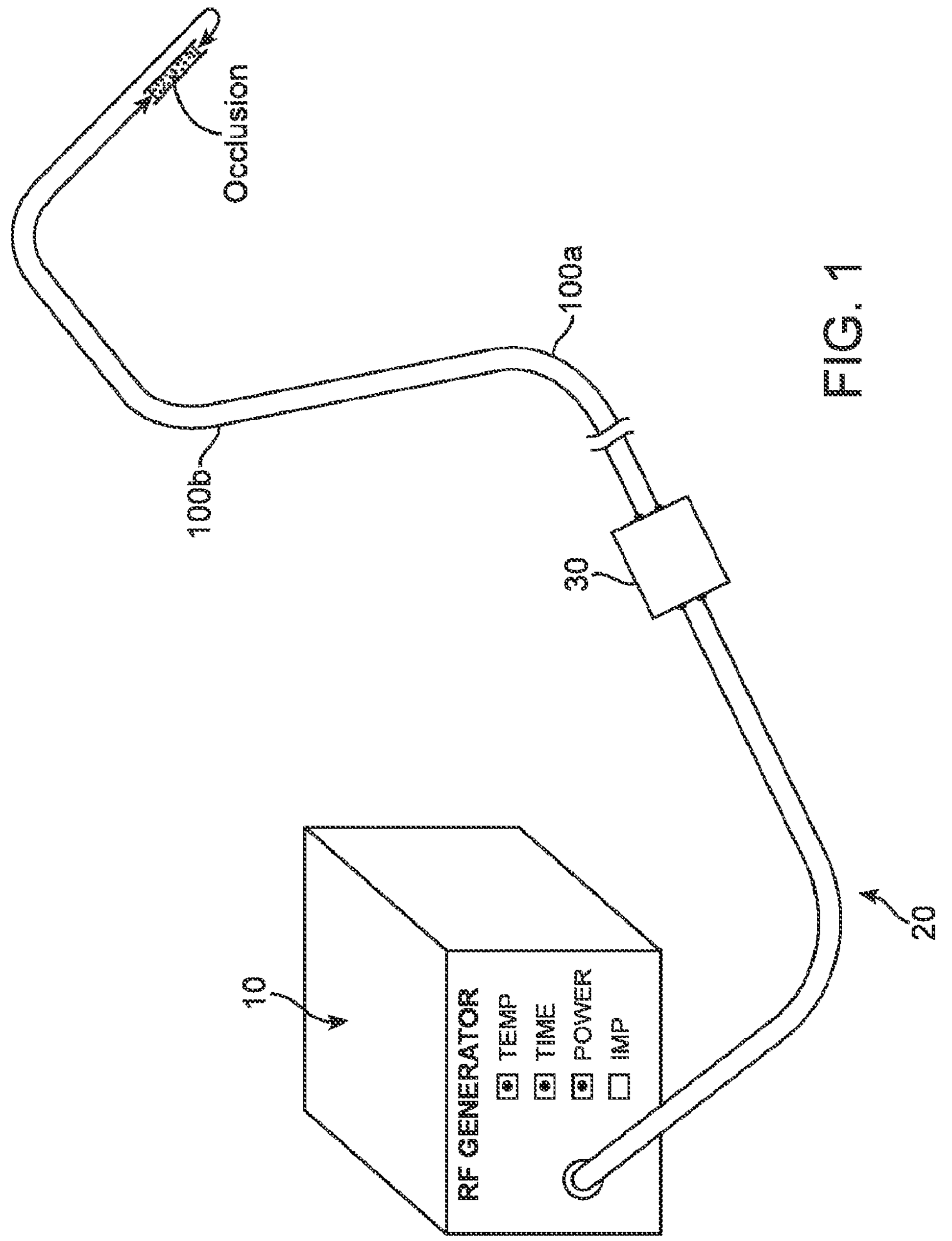
FIG. 1 is a schematic showing an RF generator connected to the longitudinal members.

Although the detailed description contains many specifics, these should not be construed as limiting the scope of the invention but merely as illustrating different examples and aspects of the invention. It should be appreciated that the scope of the invention includes other embodiments not discussed herein. Various other modifications, changes and variations which will be apparent to those skilled in the art may be made in the arrangement, operation and details of the method and apparatus of the present invention disclosed herein without departing from the spirit and scope of the invention as described here.

The present embodiments combine the use of RF energy delivered through antegrade and retrograde members for recanalizing occluded lumens, particularly chronic total occlusions. The methods and systems described herein recanalize difficult to cross occlusions by taking advantage of an antegrade and retrograde approach to establish a bipolar electrode arrangement across the occlusion. This approach minimizes the potential of the vessel wall becoming perforated or injured, as may otherwise occur in a conventional bipolar RF treatment approach, where both RF electrodes are on the same side of the occlusion. Because the electrodes are distributed on opposite sides of the occlusion, the tissue that is ablated by the RF treatment (i.e., the occlusion) is well contained between the electrodes. This also allows the user to localize the treatment to the occlusion.

As disclosed in the co-pending U.S. patent application Ser. No. 11/706,041 by the same inventors, which is incorporated herein in its entirety, in the controlled antegrade and retrograde tracking (CART) technique the retrograde approach takes advantage of an intercoronary channel. Such a channel may be an epicardial channel, an inter-atrial channel, an intra-septal channel (also referred to as septal collateral), or a bypass graft. The basic concept of the CART technique is to create a channel through an occlusion, preferably with limited dissections, by approaching the occlusion both antegradely and retrogradely.

While the combined antegrade and retrograde approach has been effective in crossing difficult to cross lesions, it has been observed that using energy, for example RF energy, to ablate or alter the tissue in a controlled fashion is beneficial in crossing hard to cross lesions. Such controlled energy deployment is achieved using a bipolar arrangement of the electrodes, where one electrode is located on the antegrade element and the other electrode that constitutes the bipolar arrangement is located on the retrograde element. These electrodes can also be referred to as the return and active electrodes. They are also referred to as the anode and cathode, respectively. The electrodes could also be arranged in an array (multiple electrodes), where the electrode arrangement provides better control over the depth of penetration of the RF field and thereby provides the ability to control the tissue temperature.

FIG. 1 shows a system for recanalizing occluded vessels using RF energy. The system comprises longitudinal members 100*a* and 100*b* for delivering RF energy to an occlusion. As indicated in FIG. 1, longitudinal member 100*a* serves as an antegrade member and longitudinal member 100*b* serves as a retrograde member. An RF generator 10 (also referred to as a controller) serves as the source of RF energy to be provided to longitudinal members 100*a* and 100*b*. Optionally, the RF generator may be a hand-held battery-operated device. Longitudinal members 100*a* and 100*b* may be guidewires, catheters, micro-catheters, or dilating catheters. In a preferred embodiment, longitudinal members 100*a* and 100*b* are guidewires. Thus, while in the following description the term "guidewire" is used to refer to a longitudinal member 100*a* or 100*b*, it is understood that the term "guidewire" as used herein is intended to include any other type of longitudinal member.

To provide RF energy from the RF generator 10 to the guidewires 100*a* and 100*b*, a pigtail 20 connects at its proximal end to the RF generator 10 and terminates at its distal end in a connector 30. Connector 30 is a standard connector that couples the input and output signals of the RF generator 10 to the guidewires 100*a* and 100*b*.

One embodiment of the connector would be a locking tool or torque device which can be placed over the guidewire. In such a configuration, the locking tool or torque device is configured to make electrical contact with a portion of the guidewire (such as the guidewire corewire) that conducts radiofrequency energy to, or from, the one or more electrodes disposed on the guidewire. In such a configuration, the locking tool or torque device would also be configured to connect to a radiofrequency generator, thereby electrically connecting the generator to the guidewire and electrodes. Means of locking the connector to the guidewire may include compressible prongs, screws, sliding rings, or other mechanisms commonly utilized in torque devices.

Guidewires 100*a* and 100*b* are configured to have sufficient torsional rigidity and longitudinal flexibility to advance through an occlusion, and to align their electrodes in a direction away from the vessel wall, towards the other guidewire, or any combination thereof.

Figure 2:
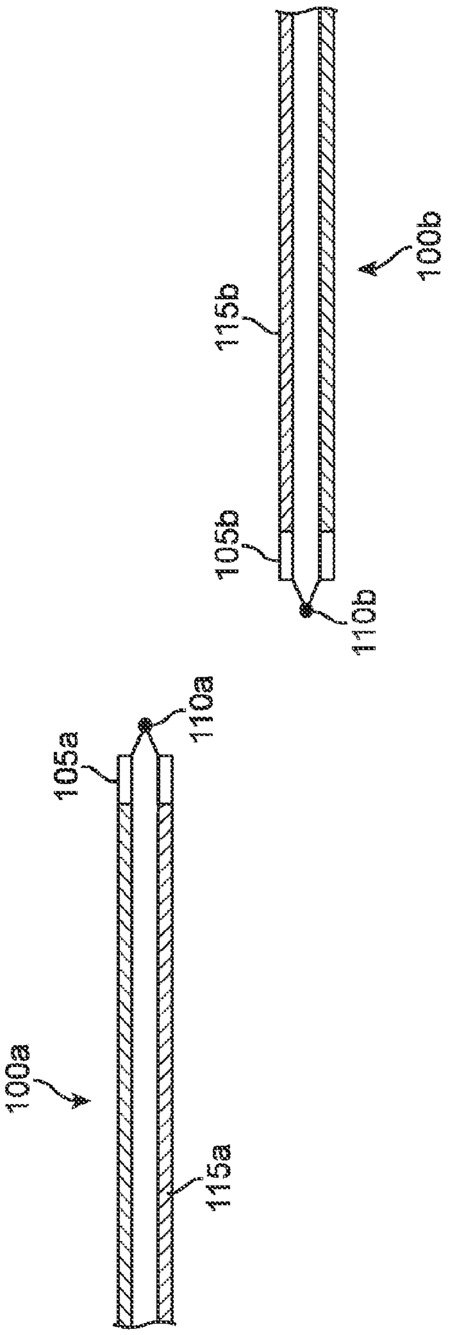
FIG. 2 shows the features of the longitudinal members.

As shown in FIG. 2, the antegrade and retrograde guidewires 100*a* and 100*b* have conductive electrodes 105*a* and 105*b*, respectively, at their distal ends. In one embodiment, the electrodes 105*a* and 105*b* are located on one side of their respective guidewires 100*a* and 100*b*, thereby providing the operating physician with the freedom to allow the electrode-free side of the guidewire to touch the vessel wall (if needed) while still directing the RF energy away from the vessel wall. Additionally, this allows the configuration to direct the RF energy away from the vessel wall, thereby minimizing potential RF injury to the vessel wall. In one embodiment, one or more of the guidewires comprises a plurality of electrodes arranged in an array.

Figure 2A:
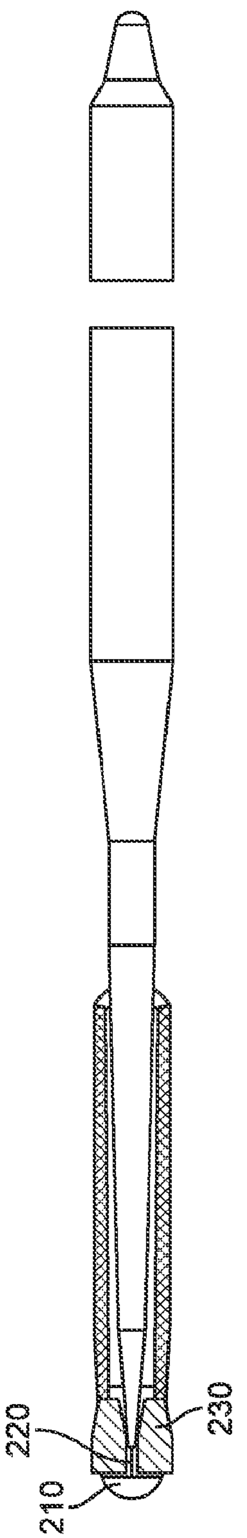
FIGS. 2A-2B show various embodiments of longitudinal members comprising insulators.

Conductive wires (not shown) connect the electrodes 105*a* and 105*b* of the antegrade and retrograde guidewires, respectively, to connector 30 to deliver RF energy from the RF generator 10 to the electrodes 105*a* and 105*b*. The exterior of the antegrade and retrograde guidewires are covered by non-conductive layers 115*a* and 115*b*, respectively, which sandwich the conductive wires between the guidewires and the non-conductive layers. In one embodiment, the non-conductive layers 115*a* and 115*b* comprise a sheath or a coating. Example of materials may include Teflon, ceramic, polyimide, parylene, or other suitable materials. Examples of methods which could be employed for coating may include spraying, dipping, vapor deposition, or plasma deposition. In another embodiment, the conductive wires are insulated by using a heat resistant material on the guidewire to protect the device and surrounding tissue from excessive heat. FIG. 2A shows a cross-sectional view of a guidewire comprising an electrode and an insulator, in accordance with an embodiment of the present invention. A guidewire 200 comprises an electrode 210 as its distal tip. The electrode 210 is electrically coupled to the guidewire's corewire via an electrically conductive ribbon 220 or other such electrically conductive connector. An insulator 230 is disposed at a distal portion of the guidewire 200 to deflect some of the heat that is generated when the electrode 210 is energized with radiofrequency energy, thereby protecting the rest of the device from such heat. The insulator 230 may wrap around the distal portion of the guidewire 200, as shown in FIG. 2A, or it may be configured as a plurality of discrete pieces disposed at the distal portion of the guidewire 200. The insulator may or may not directly contact electrodes.

Figure 2B:
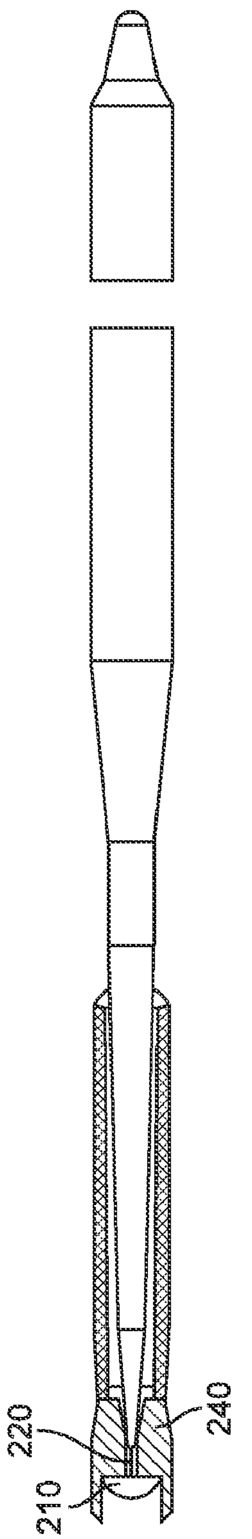

In another embodiment, the insulator may be configured to protrude forward so that the electrode is recessed. An example of this is shown in FIG. 2B, showing a protruding insulator 240 configured to extend beyond the electrode 210, thereby recessing the electrode 210. This limits the exposure of the electrode 210 to surrounding tissue, while leaving the electrode sufficiently exposed to create the bipolar arrangement.

In one embodiment, and as further shown in FIG. 2, the guidewires 100*a* and 100*b* comprise temperature measuring elements 110*a* and 110*b* at the distal tip of the antegrade and retrograde guidewires, respectively. In one embodiment, the temperature measuring elements 110*a* and 110*b* comprise thermocouples or thermistors that are connected to the connector 30. In another embodiment, pressure measuring elements are placed on the distal ends of the guidewires to detect a change in pressure upon activation of the RF energy.

RF generator 10 is configured to allow the user to set a maximum temperature, a treatment time period, a level of RF power, or a combination of these control parameters. The treatment time period indicates the period of time over which the RF energy will flow between the electrodes. The maximum temperature setting serves as a threshold temperature for the tissue that is in contact with the electrodes, and the RF generator 10 can be set to reduce or shut off power to one or both electrodes when one or more of the temperature measuring elements 110*a* and 110*b* indicate a tissue temperature at or near the threshold.

In one embodiment, the generator 10 is capable of measuring the impedance of the tissue between the two electrodes 105*a* and 105*b*. Based on the type of the occlusion (i.e., the nature of the calcified material), the user can choose the appropriate combination of temperature, treatment time, and the amount of RF energy to be provided to the tissue to achieve a safe and effective treatment. Alternatively, the treatment may proceed with the user manually controlling the parameters during the recanalization procedure, with the user treating the occlusion until recanalization is achieved.

Figure 3A:
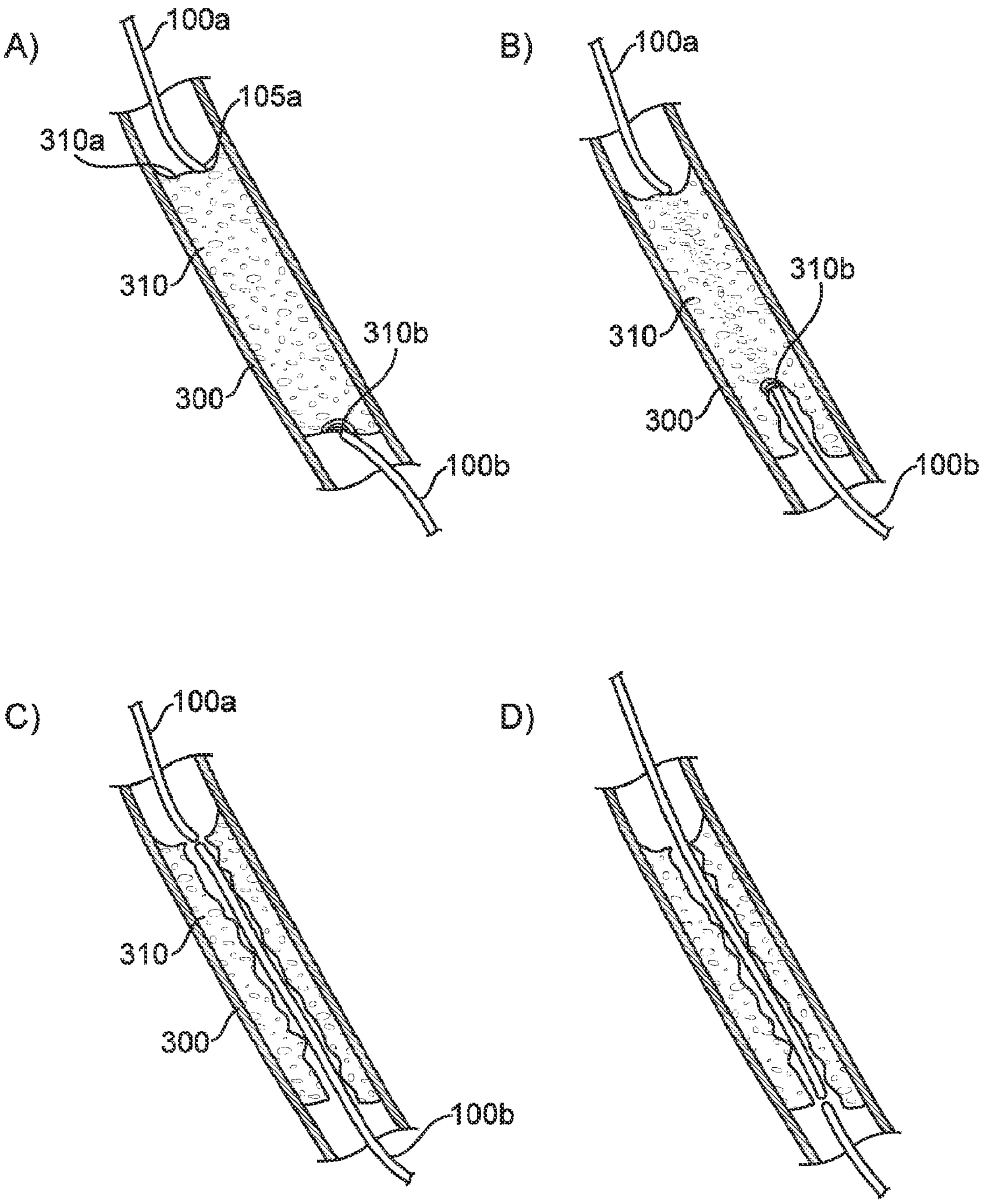
FIGS. 3A and 3B show the steps involved in recanalizing a CTO using bipolar RF and combined antegrade and retrograde approach.
Figure 3B:
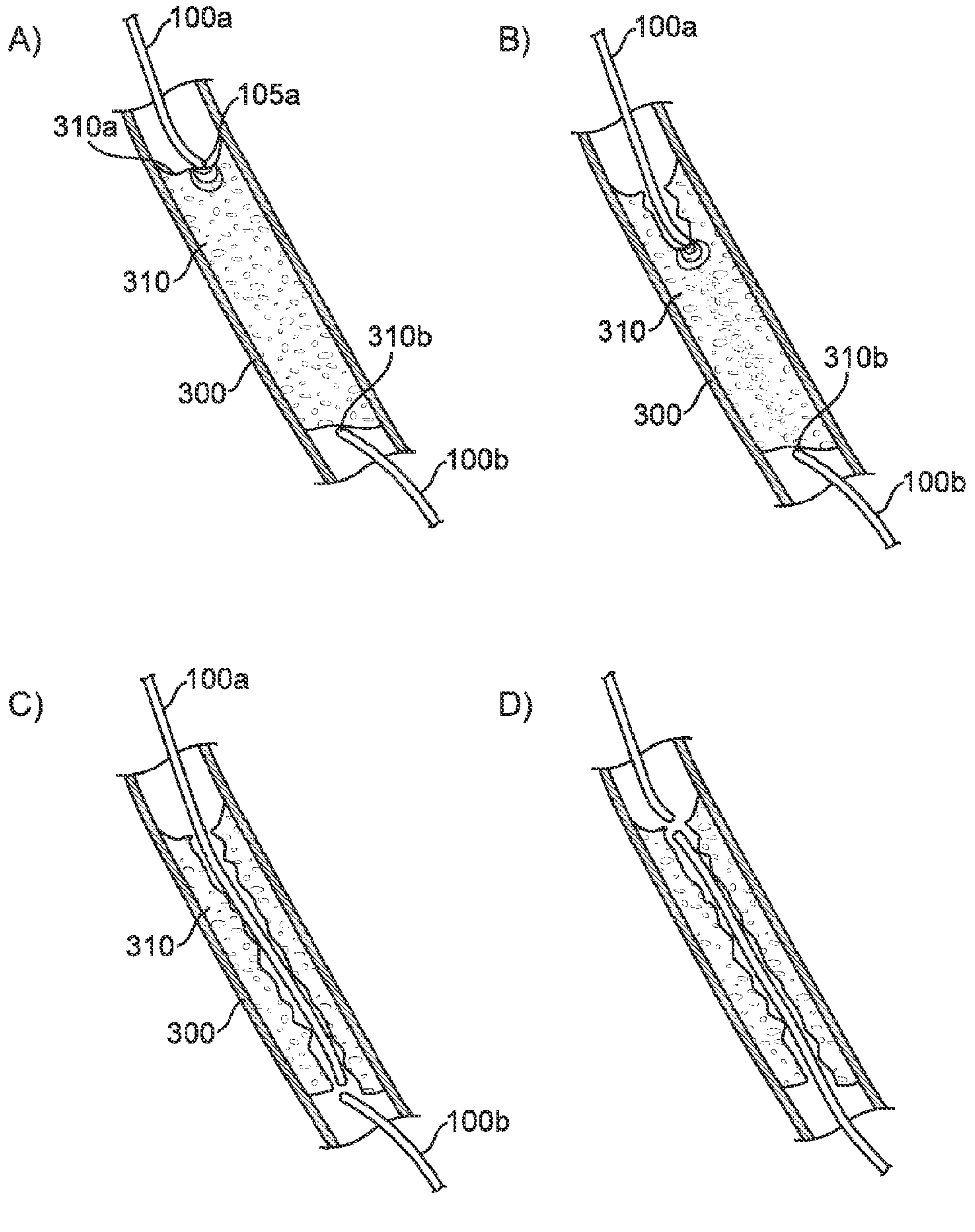

The sequence of the recanalization treatment steps are illustrated in FIGS. 3A and 3B. As shown in diagram A of FIG. 3A, the antegrade guidewire 100*a* and retrograde guidewire 100*b* are advanced to the proximal and distal ends 310*a* and 310*b* of the occlusion 310, respectively. This can be accomplished using standard angioplasty techniques. As described in the above referenced co-pending U.S. patent application Ser. No. 11/706,041, the retrograde guidewire can be advanced to the distal end of the occlusion 310*b* using collaterals such as the septals.

Once the user has confirmed that the guidewires 100*a* and 100*b* are in contact with the occlusion 310 and are not touching the vessel wall 300, the RF treatment is initiated.

Alternatively, the guidewires are advanced as deep into the occlusion as possible to minimize the distance between the electrodes and, consequently, minimize the length of the ablation zone. Confirmation that the guidewires 100*a* and 100*b* are in an appropriate position can be generated by impedance measurements and/or by using any of the standard imaging techniques employed during interventional procedures, such as fluoroscopy or intravascular ultrasound (IVUS), in which transducers are placed on the distal ends of the guidewire. When using tissue impedance measurements, the calcified occlusion 310 generally exhibits significantly higher impedance than the vessel wall 300. If an impedance measurement indicates a low impedance value, it is likely that one or both guidewires are in contact with the vessel wall 300, and appropriate repositioning of the guidewires may be warranted.

Upon initiating the recanalization RF treatment, the occlusion 310 is ablated from the ends 310*a* and 310*b* of the occlusion 310 to the interior of the occlusion 310, as shown in FIG. 3A diagram B. The user then slowly and carefully advances one or both guidewires 100*a* and 100*b* until a channel or path is created in the occlusion 310, as shown in FIG. 3A diagram C. As shown in FIG. 3A, the antegrade guidewire 100*a* may be kept stationary and the retrograde guidewire 100*b* may be advanced through the occlusion 310. Once a channel has been created, the retrograde guidewire 100*b* may be withdrawn and the antegrade guidewire 100*a* may be advanced through the occlusion 310, as shown in FIG. 3A diagram D, and standard interventional procedures, such as balloon angioplasty, can be performed. Alternatively, the retrograde guidewire 100*b* can be kept stationary during the RF treatment and the antegrade guidewire 100*a* can be advanced through the occlusion 310. This is illustrated in FIG. 3B diagrams A D.

It is noted that energizing an electrode with radiofrequency energy causes the electrode to generate heat. In general, the amount of such heat is proportional to the amount of radiofrequency energy delivered to the electrode, and inversely proportional to the surface area of the electrode. This is because the smaller the surface area of an electrode, the higher the current density passing through that surface area (for a given total current), which in turn causes the electrode to reach correspondingly higher temperatures. In one embodiment, the system is configured to deliver sufficient radiofrequency energy to an electrode such that radiofrequency sparks are generated.

While it is possible to have the surface areas of the active and return electrodes be of similar size, in a preferred embodiment an active electrode is configured to have a smaller surface area than a return electrode. This allows the active electrode to generate sufficient current or energy density to affect cutting or ablating and spark cover to the return electrode, while at the same time allowing the return electrode surface area to be sufficiently large so as to maximize its contact with the occlusion and act as a sink for the energy emitted from the active electrode. Another advantage of such an embodiment is that the return electrode will likely not reach as high temperatures as the active electrode. In one embodiment, the ratio of the return electrode surface area to the active electrode surface area is configured to be in the range of about 50:1 to about 1:1, and preferably about 10:1. In one embodiment, the return electrode is configured in a pigtail design to increase surface area contact with the occlusion.

Figure 3C:
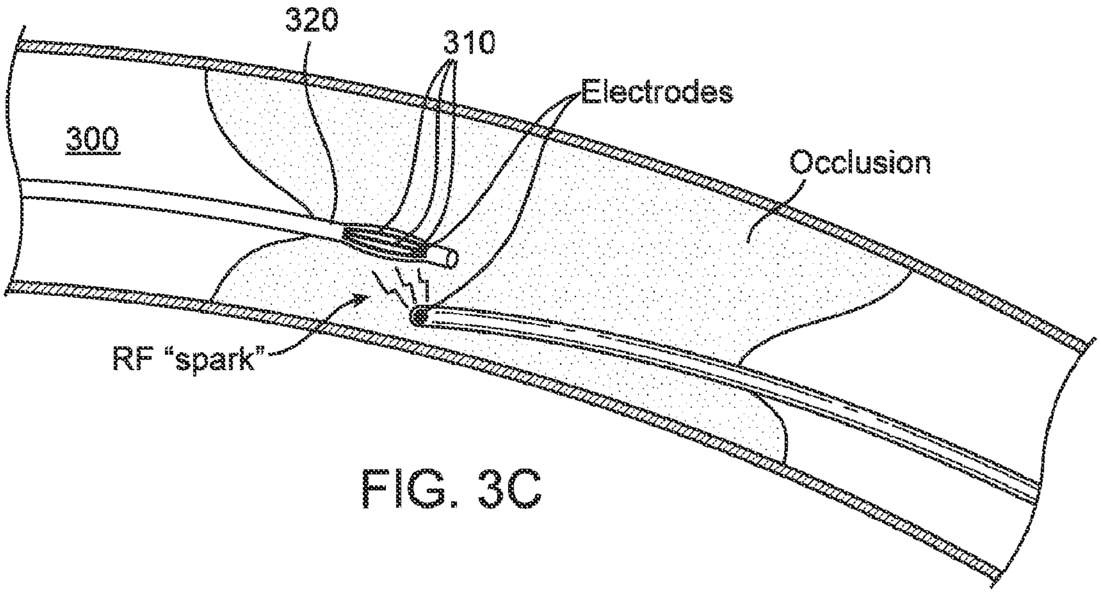
FIGS. 3C-3E show embodiments of electrodes configured to expand outwardly.
Figure 3D:
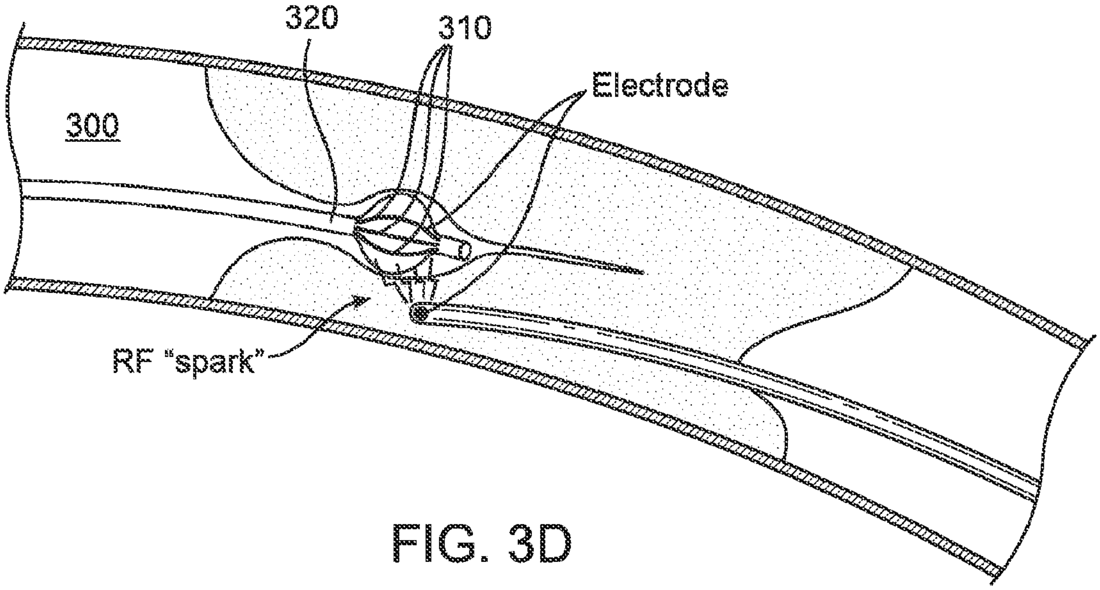

In another embodiment, a plurality of return electrodes may be configured to expand outwardly in order to spread out and increase surface area contact with the occlusion. Such an embodiment is shown in FIG. 3C, where a plurality of ribs 310 are disposed on a distal end 320 of a guidewire 300. The ribs 310 are configured to flare out, as shown in FIG. 3D. In a collapsed state, the ribs 310 are kept under tension, for example by using a restraining sleeve (not shown), by twisting the ribs 310, by exerting a stretching or pulling force on the proximal ends of the ribs 310, etc. The guidewire 300, with the ribs 310 in a collapsed state, is advanced into the occlusion. Upon releasing the tension or pulling back on the restraining sleeve, the ribs 310 flare open.

Figure 3E:
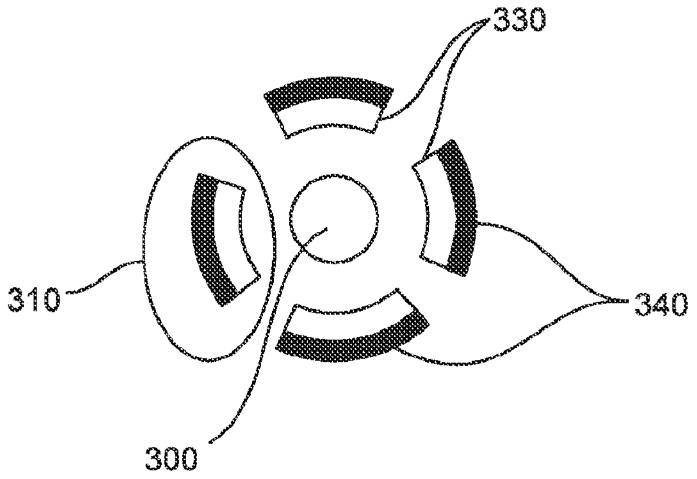

In another embodiment, the ribs 310 comprise electrode areas 330 adjacent to insulator areas 340, as shown in the cross-sectional view of FIG. 3E. In such an embodiment, when the ribs 310 flare out into a basket-like configuration, the insulator areas 340 are on the outside and the electrode areas 330 are on the inside of the basket-like configuration. This configuration advantageously aids in directing radiofrequency energy inside the basket-like configuration while simultaneously providing protection to the surrounding tissue. Alternatively, it is contemplated that in other embodiments the placement of the electrode areas 330 and insulator areas 340 may be varied. In an optional embodiment, a capture device may be configured to comprise one or more electrode areas for use as return electrodes. Examples of capture devices are disclosed in the co-pending U.S. patent application Ser. No. 12/150,111 by the same inventors, which is incorporated herein in its entirety.

Optionally, a centering balloon catheter can be utilized along with the guidewire to center the guidewire within the vessel prior to energizing the system. In such a configuration, it would be advantageous to have a heat resistant tip on the distal end of the balloon catheter.

Figure 4:
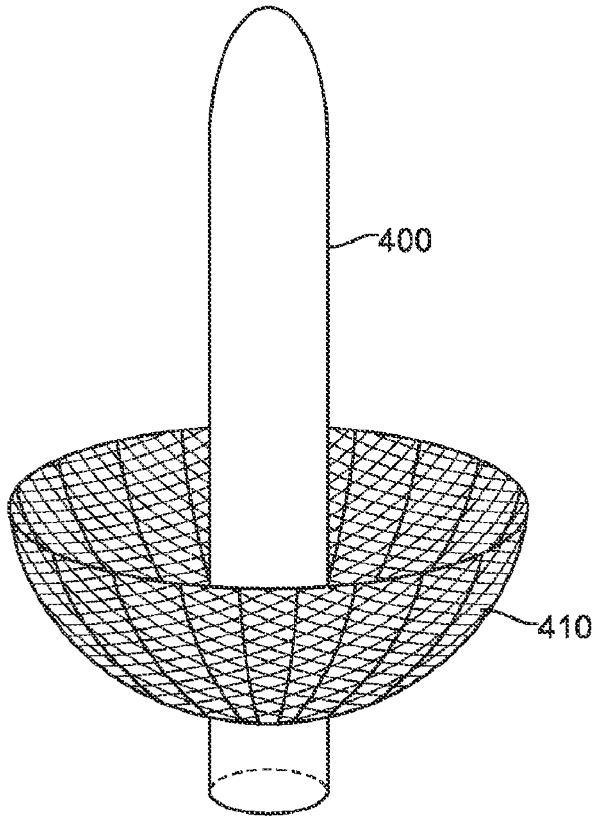
FIG. 4 shows an example embodiment of a longitudinal member comprising an embolic protection mechanism.

Optionally, the catheter comprises a means for removing or withdrawing debris resulting from the RF ablation. For example, a mechanism could be provided to capture and retrieve the debris, or a suction device could be provided to actively remove the debris near the ablation area. Examples of such embolic protection mechanisms are disclosed in the above referenced co-pending U.S. patent application Ser. No. 11/706,041. FIG. 4 shows an exemplary embodiment of a longitudinal member 400 comprising an embolic protection mechanism 410. The embolic protection mechanism 410 comprises a filter, mesh, net, or similar element, for capturing and retrieving ablation debris. As another example, the embolic protection may comprise a balloon for occluding the vessel and preventing the debris from circulating, and for subsequent aspiration of the debris through a longitudinal member. As another example, if a sheath is provided, such sheath may also be configured to be or to include a debris capture and retrieval mechanism or a suction device. In one embodiment, a longitudinal member may be retracted, and the remaining sheath may be used as a capture and retrieval mechanism or a suction device to remove ablation debris. In another embodiment, the longitudinal member comprises an ablating wire housed in the lumen of a dilating catheter. Upon ablation, the ablating wire may be retracted and the dilating catheter may be used to remove the debris. Alternatively, the system comprises a separate catheter to provide suction, or otherwise capture and remove the debris from the ablation site.

Optionally, the device may be coupled to an electrocardiogram (EK G) machine to aid in timing energy emissions. For example, the rate of blood flow through the coronary arteries typically varies during the cardiac cycle. During systole when the heart is contracting, flow through the arteries is generally lower than during diastole. In one embodiment, energy emission is timed during diastole, for example using an algorithm to detect the R-wave of an EK G, and energy emission is timed to occur when flow is highest, thereby maximizing the cooling effect provided by blood flow and consequently minimizing the heat exposure to the vessel. Additionally, coronary artery dimensions can vary during the cardiac cycle and energy emission can similarly be timed to take advantage of this fact.

Optionally, the device may be configured to perform an imaging function, such as intravascular ultrasound or optical coherence tomography (OCT). In one embodiment, this may be accomplished by adding a piezoelectric crystal to a longitudinal member of the device, wherein the piezoelectric crystal may be energized to transmit or receive ultrasonic waves. In another embodiment, an imaging core may be inserted into a longitudinal member of the device (e.g., in the case of a dilating catheter) and operated to transmit and receive ultrasonic waves. In another embodiment, an optical fiber may be used for performing OCT imaging.

Optionally, the device comprises a mechanism for detecting or estimating the distance between the electrodes, and for decreasing the amount of delivered RF energy as the distance between the electrodes decreases, thereby minimizing potential RF injury to the vessel wall.

Figure 5A:
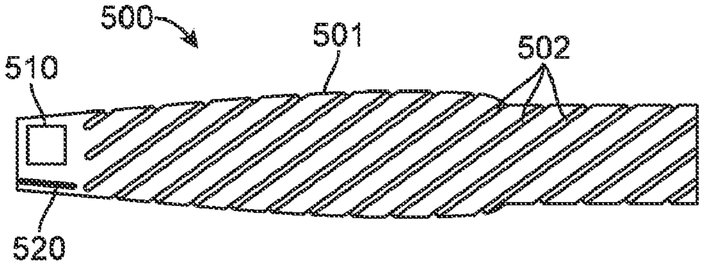
FIGS. 5A-5C show a longitudinal member structurally configured along at least part of the length of the catheter to enable advancement or alignment of the longitudinal member through a narrow diameter blood vessel or occlusion.
Figure 5B:
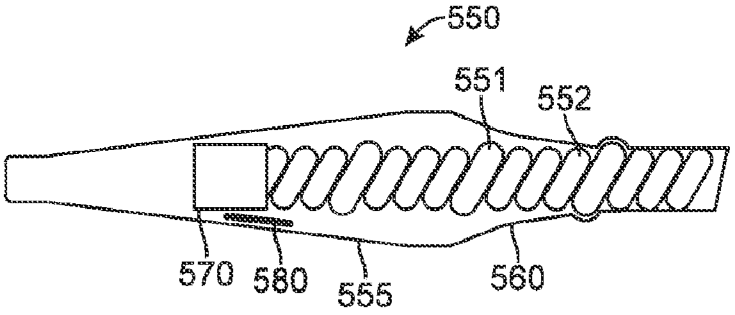
Figure 5C:
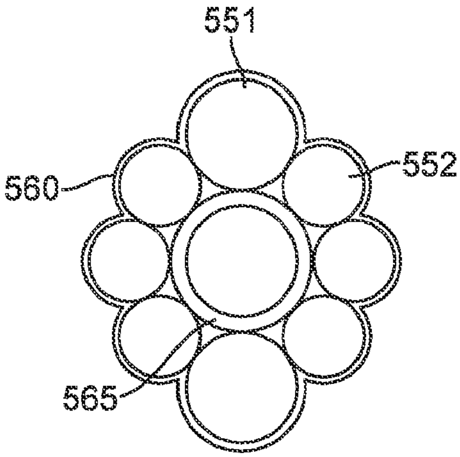

In another embodiment, the device is an ablation catheter comprising a longitudinal member having a distal end, a proximal end, and a guidewire shaft there-between comprising a guidewire lumen. The longitudinal member is a dilating catheter and is structurally configured along at least part of the length of the catheter to enable advancement or alignment of the longitudinal member through a narrow diameter blood vessel or occlusion. Advancement is achieved, for example, by turning or twisting the longitudinal member. FIGS. 5A-5C show such an embodiment of the present invention. For example, as shown in FIG. 5A, the longitudinal member 500 may comprise a helical exterior 501 that advances through the vessel and dilates the vessel as the member is being twisted or rotated. Helical exterior 501 comprises a plurality of grooves 502 carved into the outer body of the longitudinal member 500. The distal tip of longitudinal member 500 optionally comprises a radiopaque marker 510. An electrode 520 is located at or near the distal end of the catheter. Another example is shown in FIG. 5B, the cross section of which is shown in FIG. 5C. The longitudinal member 550 may comprise a plurality of wires 551 and 552 wound around a liner 565. In one embodiment, the wires 551 and 552 comprise at least two different cross-sectional diameters. Longitudinal member 550 optionally terminates at a marker 570. An electrode 580 is located at or near the distal end of the longitudinal member 550. The ablation catheter additionally and optionally comprises conductive wires for transmitting energy between the electrode and an external energy source. Alternatively, the plurality of wires may be configured to act as the electrode or conductive wires. Additionally and optionally, the catheter comprises an insulating sheath 560 which is optionally retractable.

The guidewires and electrodes may be made from any one or more suitable materials as is commonly known in the art. Examples of such suitable materials include stainless steel, Nitinol, Elgiloy, platinum, iridium, tantalum, titanium, cobalt, chromium, tungsten, or any combinations thereof. In one embodiment, one or more of the guidewires may be made of a polymer, with an electrically conductive core for transmitting electrical energy to the respective electrodes.

Additional embodiments disclosed here comprise of methods, systems, and devices to recanalize an occluded body vessel by penetrating the distal cap of the occlusion without approaching the distal cap from the retrograde direction through an intercoronary channel; thereafter, RF energy may be delivered in a biopolar arrangement between two longitudinal members as described above.

Figure 6:
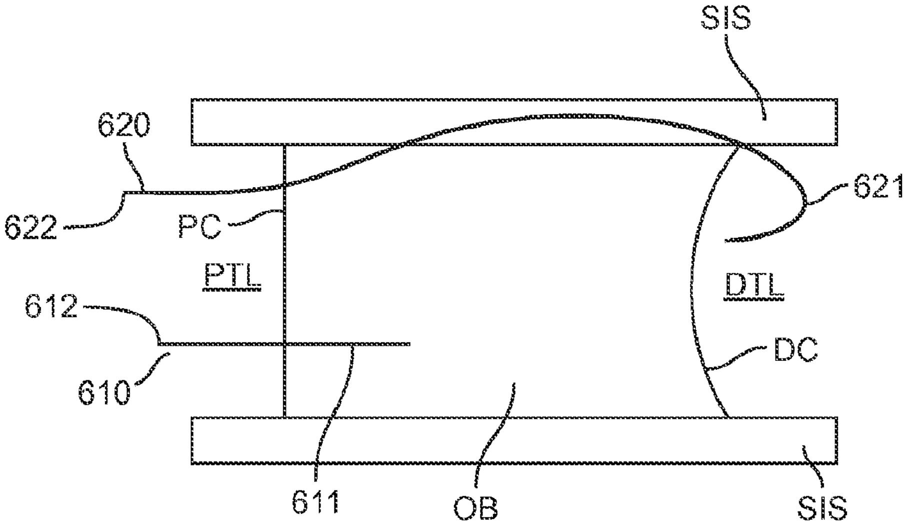
FIG. 6 shows one embodiment of the recanalization system comprising a longitudinal member that is capable of being redirected.

Referring now to FIG. 6, where one embodiment of the device is shown: The device comprises a first longitudinal member 610 and a second longitudinal member 620. The first longitudinal member 610 comprises a first distal end 611 and a first proximal end 612. In one embodiment, the first distal end 611 may be configured to penetrate the proximal cap PC of an occlusion such that the first longitudinal member 610 may advance at least partly into the occlusion body OB from the proximal true lumen PTL in an antegrade fashion. The second longitudinal member 620 comprises a second distal end 621 and a second proximal end 622. In one embodiment, the second distal end 621 may be configured to penetrate a portion of the occluded body vessel BDL such as the proximal cap PC or a portion of the subintimal space SIS. The second longitudinal member 620 may advance at least partly into the occlusion body OB from the proximal true lumen PTL in an antegrade fashion. Alternatively, the second longitudinal member 620 may advance through the subintimal space SIS without traversing through the occlusion body OB.

The second distal end 621 may be further configured to be capable of being redirected. In one embodiment, the second distal end 621 may be redirected once the second longitudinal member 620 has at least traversed the length of the occlusion body OB and/or otherwise has entered the distal true lumen DTL. Whereupon redirection, the second distal end 621 may be positioned such that the second distal end 621 may be configured to penetrate the distal cap DC of the occlusion.

The redirection of the second distal end 621 may be accomplished through various methods. In one embodiment, the device may comprise one or more strings (not shown) attached to the second distal end 621, wherein a user may manipulate the strings to mechanically redirect the second distal end 621. In another embodiment, a portion of the second distal end 621 may be constructed of various shape memory alloys and the second distal end 621 may be redirected by exploiting properties of the shape memory alloys. For example, a portion of the second distal end 621 may comprise heat memory alloys, wherein the second distal end 621 is configured to be redirected when it is sufficiently exposed to an elevated temperature environment such as the human body. Alternatively, the second distal end 621 may be pre-shaped or may comprise magnetic shape memory alloy, electric shape memory alloy, etc.

It is contemplated that the various redirection methods described above may be implemented in combination. For example, the second distal end 621 may comprise one or more shape memory alloy types. Furthermore, the second distal end 621 may comprise one or more shape memory alloy types and may also be subject to mechanical manipulation, such as by strings as described above.

It is further contemplated that the present embodiments may be combined with the use of various energy modalities. For example, RF energy may be delivered through the first and the second longitudinal members. Specifically, in one embodiment where an energy modality is used to recanalize the occlusion body OB, the first and the second distal ends 611 and 621 may each comprise at least one electrode such that controlled energy deployment is achieved using a bipolar arrangement of the electrodes as described above.

Figure 7:
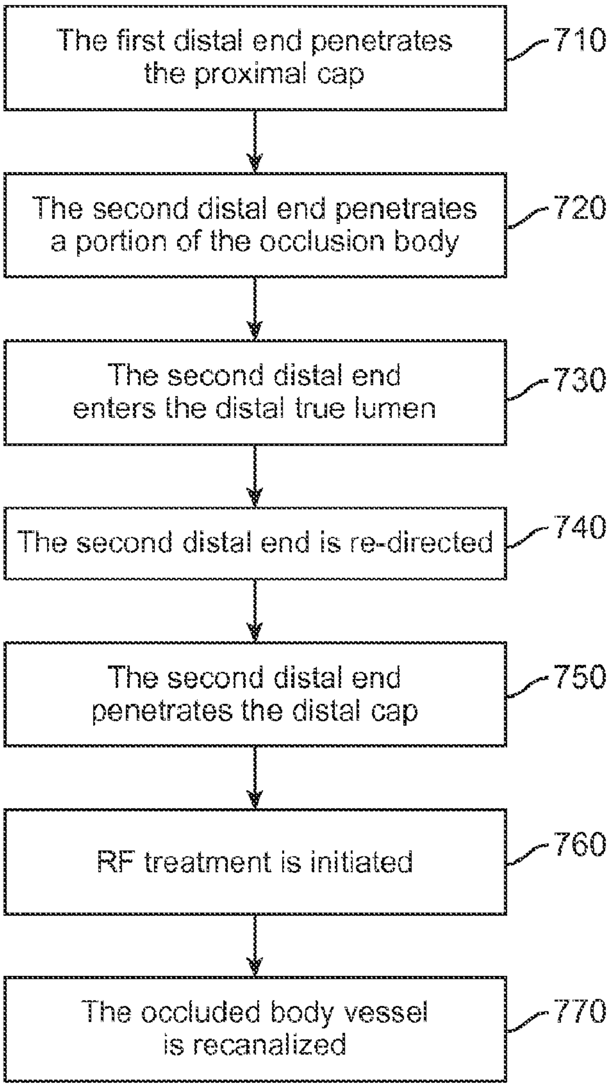
FIG. 7 shows a flow diagram of various steps involved in performing the recanalization of the body vessel according to the present embodiments.
Figure 8A:
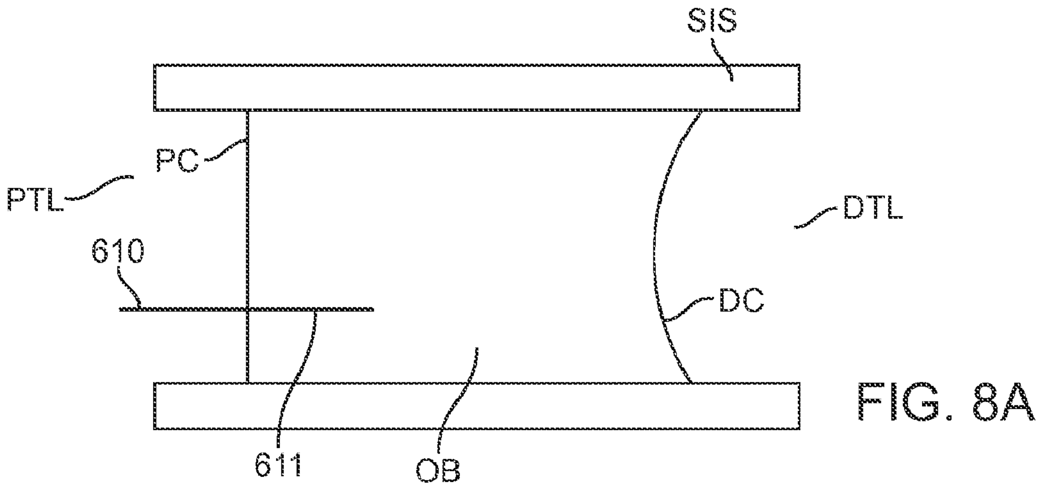
FIGS. 8A-8F show various stages of recanalization of the body vessel according to the present embodiments.

The method of recanalization using one aspect of the present embodiments is shown schematically as a flow diagram in FIG. 7 with reference to FIGS. 8A-8F. At step 710, the first distal end 611 of the first longitudinal member 610 penetrates the proximal cap PC and at least a portion of the first longitudinal member 610 is advanced into the occlusion body OB in an antegrade fashion as seen in FIG. 8A.

Figure 8B:
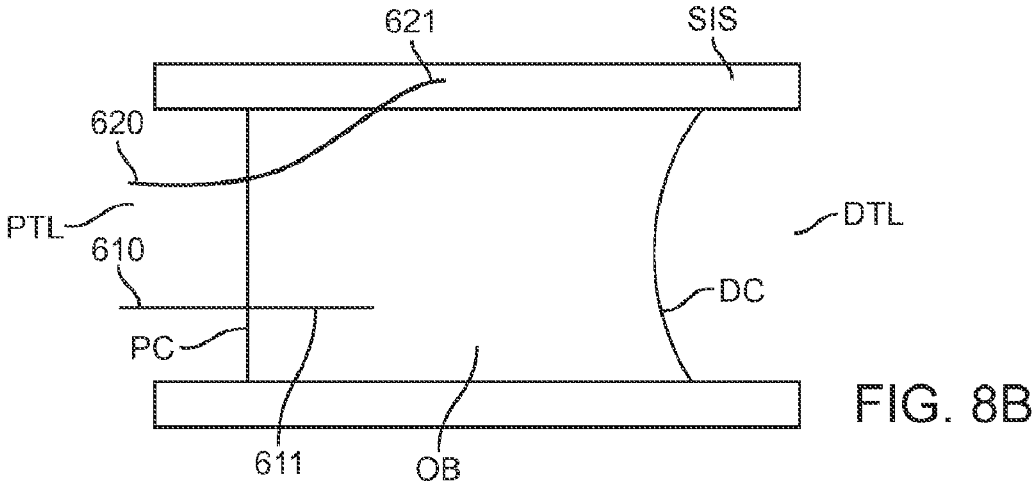

At step 720, the second distal end 621 of the second longitudinal member 620 penetrates a portion of the occluded body vessel BDL. Thereafter, at least a portion of the second longitudinal member 620 is advanced into a body region of, or close to the occlusion. As seen in FIG. 8B, the second distal end 621 may penetrate the proximal cap PC and the second longitudinal member 620 may advance through a portion of the occlusion body OB. Alternatively, the second distal end 621 may penetrate a site within the proximal true lumen PTL such as the subintimal space SIS near the proximal cap PC. Thereafter, as seen in FIG. 8B the second longitudinal member 620 may then enter and advance through the subintimal space SIS.

Figure 8C:
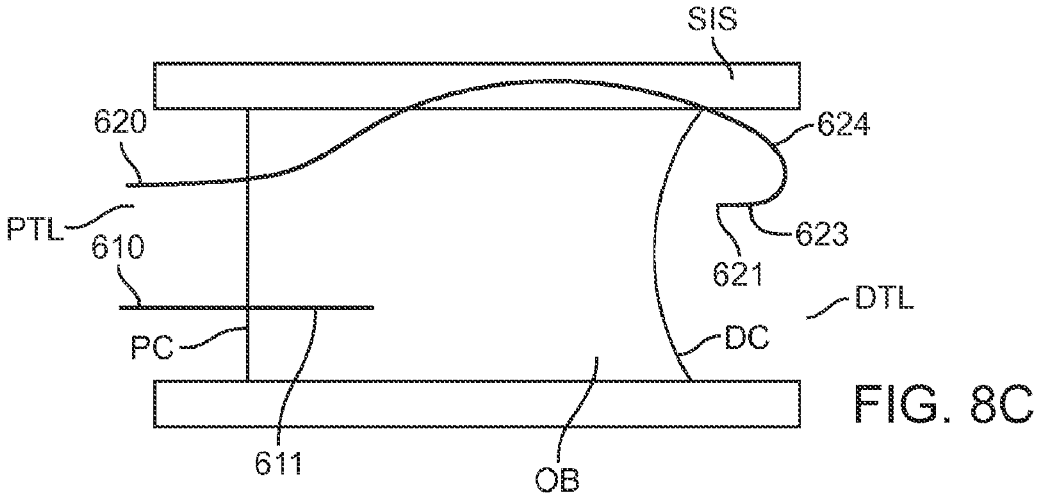

At step 730 and as seen in FIG. 8C, the second longitudinal member 620 may traverse at least the length of the occlusion body OB and it is advanced into the distal true lumen DTL through the subintimal space SIS. Alternatively, the second longitudinal member 620 may be advanced in an antegrade fashion through a portion of the subintimal space SIS without traversing a portion of the occlusion body OB.

Thereafter, at step 740 and as seen in FIG. 8C the second distal end 621 is redirected such that the second distal end 621 is configured to be capable of penetrating the distal cap DC. In one embodiment, a first portion 623 of the second longitudinal member 620 comprising the second distal end 621 is re-configured such that the first portion 623 is at an angle with respect to a second portion 624 of the second longitudinal member 620. The angle may be configured as any angle wherein the second distal end 621 is positioned such that it is capable of penetrating the distal cap DC.

Figure 8D:
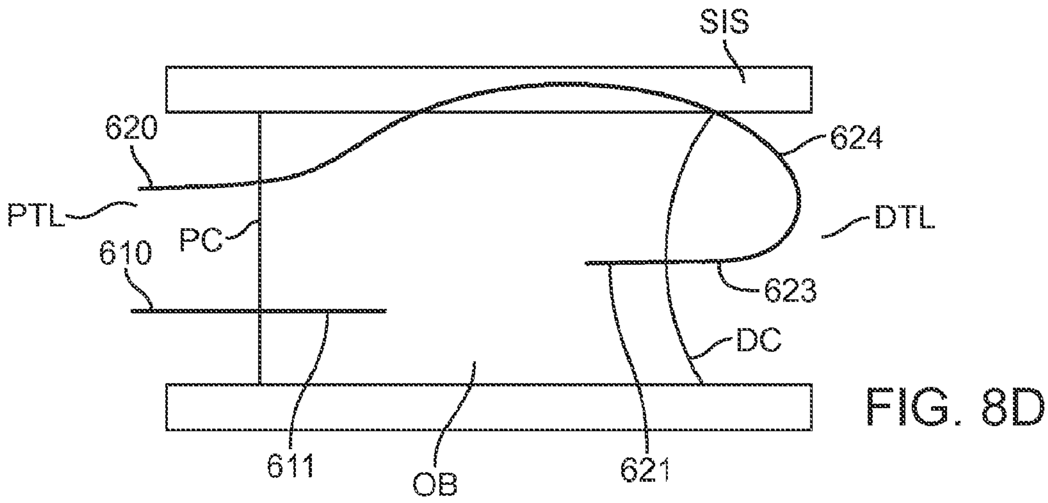
Figure 8E:
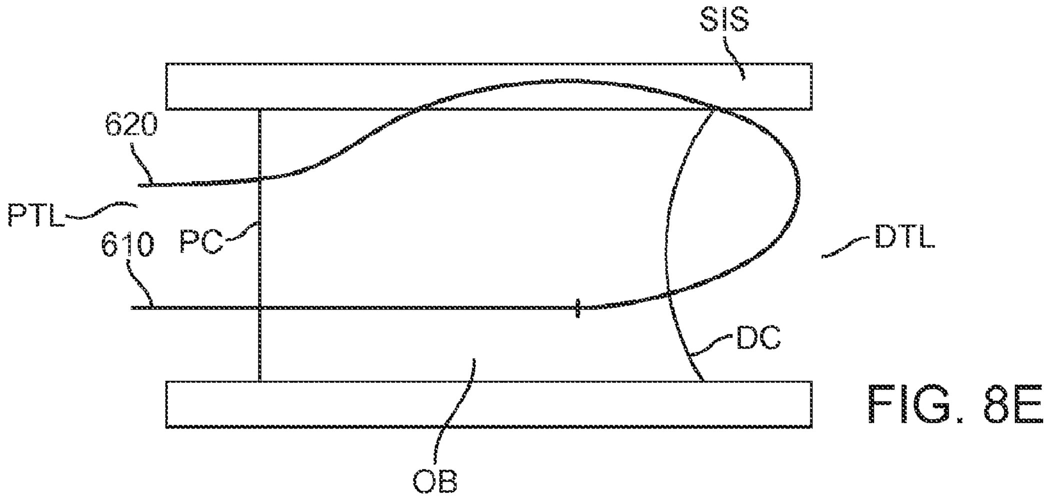

At step 750 and as seen in FIG. 8D, the second distal tip 621 penetrates the distal cap DC and at least a portion of the second longitudinal member 620 is advanced into the occlusion body OB in a retrograde fashion. In one embodiment, the second longitudinal member 620 is advanced into the occlusion body OB until it is positioned at or near the first distal end 611 of the first longitudinal member 610. In an embodiment where RF energy is used to recanalize the occlusion body OB, the electrodes disposed on the first and the second distal ends 611 and 621 may be positioned substantially towards each other. Furthermore, it is desirable that the electrodes are in contact with the occlusion body OB but are not in contact with the vessel wall to prevent or minimize damage to the vessel wall. Thereafter, at step 760, RF treatment may be initiated to create a recanalization channel.

It is noted that in an embodiment where RF energy is delivered through the first and the second longitudinal members, it may not be required for the second distal end 621 of the second longitudinal member 620 to penetrate the distal cap DC and to advance into the occlusion body OB in a retrograde fashion. In fact, it may be sufficient for the second distal end 621 and the first distal end 611 to be positioned within proximity where the radiofrequency spark may cross from the active electrode disposed on one longitudinal member to the return electrode disposed on the other longitudinal member to achieve ablation. For example, the second distal end 621 of the second longitudinal member 620 may be positioned within the distal true lumen DTL, and the first distal end 611 of the first longitudinal member 610 may be positioned within the occlusion body OB, RF energy may then be delivered between the active and return electrodes disposed on the two distal ends to ablate a portion of the occlusion body OB in between the two distal ends.

Additionally and optionally, as seen in FIG. SE, the first and the second longitudinal members may be coupled by using one or more coupling elements (not shown) such that the two longitudinal members may create a recanalization channel between the proximal and distal ends of the occlusion body OB. Furthermore, the controlled antegrade and retrograde tracking (CART) techniques disclosed in the co-pending U.S. patent application Ser. No. 11/706,041 as referenced above may be used to facilitate the coupling.

The coupling element may be configured to securely lock the first longitudinal element and the second longitudinal element to prevent separation during the guidewire placement procedure. Additionally and optionally, the coupling element may be configured to provide quick and easy detachment of the two longitudinal elements. In one embodiment, the coupling element may comprise a screw mechanism. In another embodiment, the coupling element may comprise a male portion disposed on the distal end of either the first or the second longitudinal member, and a female portion disposed on the distal end of the other longitudinal element, wherein the male portion is configured to be inserted into the female portion. In one embodiment the male portion can be spring loaded to more securely attach inside the female portion. In another embodiment, the coupling element may comprise a flaring rib mechanism in which one longitudinal element is snared by the other longitudinal element as described in the co-pending U.S. patent application Ser. No. 12/150,111 as referenced above. Alternatively, coupling may be achieved by other means of coupling, connecting, or extending longitudinal members such as the use of magnets where the distal ends of the first and the second longitudinal members comprise magnets of opposite polarity.

Thereafter, the coupled longitudinal members advance in either the antegrade or retrograde direction through the occlusion body OB until one longitudinal member traverses the occlusion body OB and a portion of it is positioned within the true distal lumen DTL.

Figure 8F:
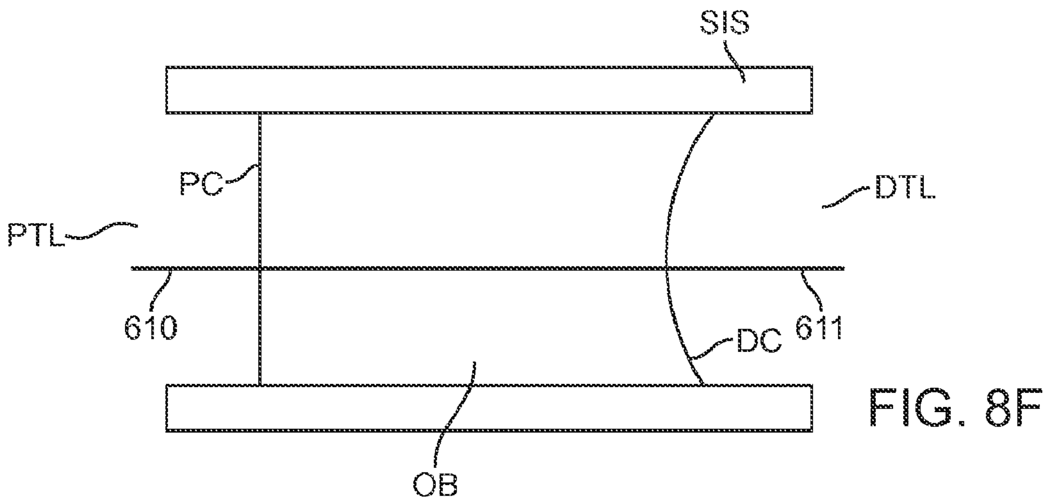

As seen in FIG. 8F, in an embodiment where the coupled longitudinal member is advanced in the antegrade direction, the first longitudinal member 610 is positioned in an antegrade direction through the occlusion body OB. Thereafter, the first longitudinal member 610 and the second longitudinal member 620 may be decoupled, and the second longitudinal member 620 may be removed from the body.

Figure 9A:
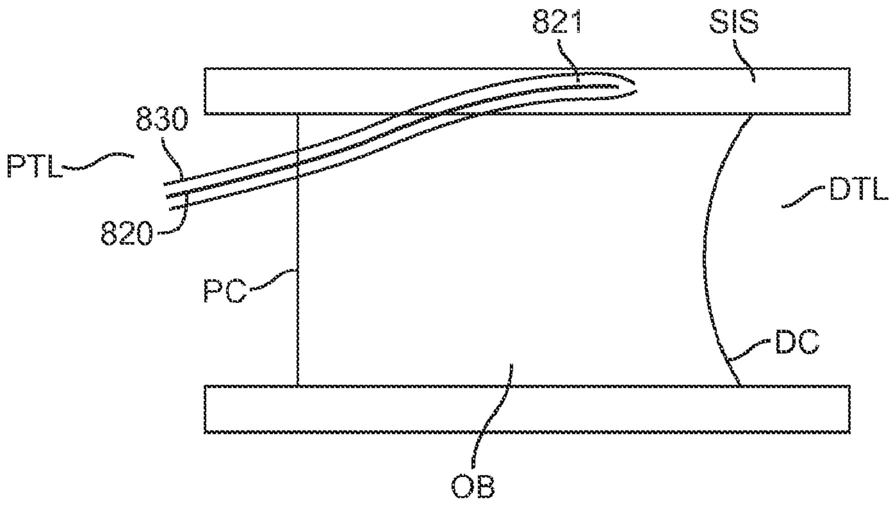
FIGS. 9A-9B show one embodiment of the recanalization system comprising a delivery element.
Figure 9B:
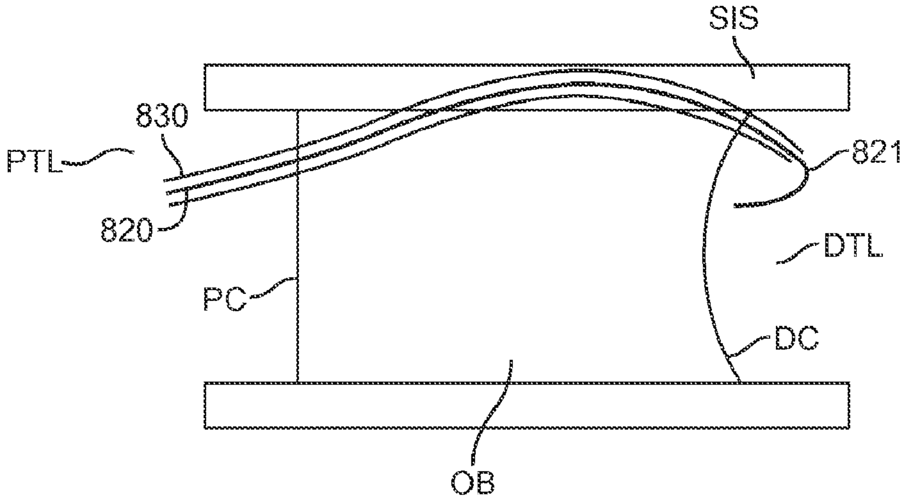

At step 770, once a recanalization channel has been created over the wire recanalization techniques that are well known in the art can be performed either in the antegrade fashion or the retrograde fashion to recanalize the occluded body vessel BDL, for example, a balloon catheter for performing an In another embodiment, the second longitudinal member may be delivered into the distal true lumen DTL from an antegrade direction using a delivery element. As seen in FIG. 9A, the second longitudinal element 820 may be inserted into a delivery lumen of the delivery element 830. The delivery element 830 may be a delivery catheter, microcatheter, a dilating catheter, a guiding catheter, or the like. The delivery element 830 then traverses the length of the occlusion body OB as described above. Thereupon reaching the distal true lumen DTL, as seen in FIG. 9B the second longitudinal member 820 is advanced through the delivery lumen. In such embodiment, the distal end of the second longitudinal member 820 may be pre-shaped such that the distal end 821 may not need to be redirected in order to penetrate the distal cap DC. Alternatively, the degree of redirection needed to position the distal end 821 of the second longitudinal member 820 may be decreased in comparison to an embodiment where the second longitudinal member 820 is inserted into the body without a delivery element 830.

In one embodiment, at least a portion of the pre-shaped distal end 821 may comprise Nitinol or other shape memory alloys such that the second longitudinal member 820 may be compressed when loaded into the delivery element 830. Upon reaching the distal true lumen DTL, the compression may be relieved when the second longitudinal member 820 is advanced through the delivery element 830 and the distal end 831 may then assume the pre-shaped configuration.

The delivery element 830 may further comprise an aspiration element (not shown) configured to remove debris products, such as debris produced by the RF treatment. In one such embodiment, the aspiration element comprises an aspiration port disposed on the distal end of the delivery element 830, and an aspiration lumen connecting the aspiration port and the aspiration source. The debris products may be removed through the aspiration port through pressure differentials generated between the aspiration port and the aspiration source, such that debris products may be transmitted through the aspiration port and are thereby removed. In one embodiment, the delivery lumen may be configured as the aspiration lumen, in another embodiment, the aspiration lumen may be a substantially independent lumen disposed within the delivery element 830.

It is contemplated that the distal ends of the first longitudinal member, the second longitudinal member, and/or the delivery element can assume any configurations that enable the first and/or the second distal ends to penetrate the distal cap DC, the subintimal space SIS, and/or any other region of the occluded blood vessel BDL. In one embodiment, one or both distal ends of the longitudinal members and/or the distal end of the delivery element may be configured as deflectable tips. In another embodiment, the distal ends of the longitudinal members or the delivery element may be configured as bevel tips. It is further contemplated that the distal ends of the longitudinal members or the delivery element may be configured as heated tips, whereby the thermal energy radiating from the heated tips may ease the penetration and/or the advancement of the longitudinal members.

Additionally, a cross-sectional area of the longitudinal members and/or the delivery element may be configured to progressively increase from the distal end towards the proximal end. The tapered configuration may be advantageous in that the narrow distal end may be configured to effectively traverse through the vascular matrix and to penetrate the occlusion and/or the subintimal space SIS, whereas the larger proximal end is configured to allow a user to manipulate the longitudinal members during the operation. Alternatively and optionally, a cross-sectional area of the longitudinal members may be configured to be substantially unchanged throughout the lengths of the longitudinal members.

It is noted that the flexibility of the longitudinal members may vary over their respective lengths. In one embodiment, the distal ends may be substantially flexible, and the flexibility progressively decreases towards the proximal ends.

Optionally, the longitudinal members of the present embodiments may comprise at least a layer of structural polymer over the core wire. Additionally and optionally, an outer surface of the longitudinal members may be coated with hydrophilic coating for ease of navigation through tortuous passageways.

Figure 10:
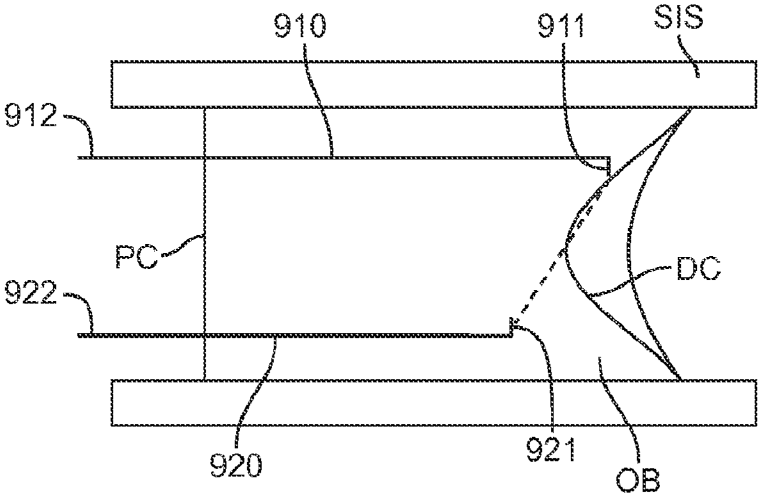
FIG. 10 shows one embodiment of the recanalization system utilizing radio frequency energy.

In another embodiment, as seen in FIG. 10, both the first and the second longitudinal members 910 and 920 may be advanced in an antegrade fashion into the occlusion body OB. The first and the second distal ends 911 and 921 of the longitudinal members can be configured to be redirected such that the first distal end 911 is directed substantially towards the second distal end 921 and/or the second distal end 921 may be directed substantially towards the first distal end 911. The redirection may be accomplished through various methods described above. This approach minimizes the potential of the vessel wall becoming perforated or injured, as may otherwise occur in a conventional bipolar RF treatment approach. Because the electrodes are positioned towards each other, the tissue that is ablated by the RF treatment (i.e., the occlusion) is well contained between the electrodes. This also allows the user to localize the treatment to the occlusion while minimizing vessel wall damage.

Figure 11:
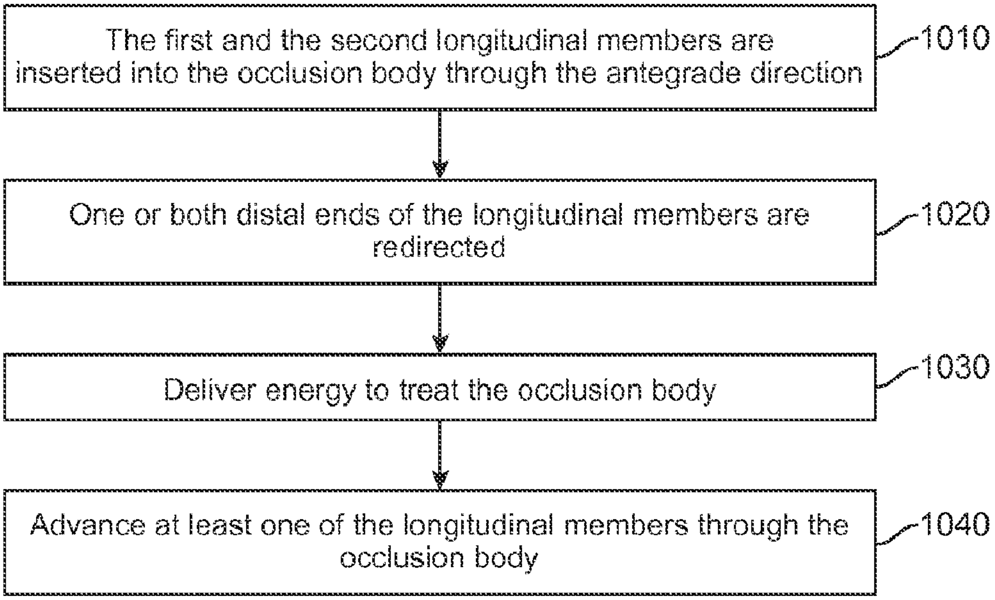
FIG. 11 shows a flow diagram of various steps involved in performing the recanalization of the body vessel utilizing radio frequency energy.

The sequence of the recanalization treatment steps where both the first and the second distal ends of two longitudinal members are redirected are illustrated in FIG. 11 as a flow diagram. At step 1010, the first and the second longitudinal members 910 and 920 are advanced through the proximal cap PC into the occlusion body OB in an antegrade fashion.

The longitudinal members may be advanced as deep into the occlusion body as possible to minimize the distance between the electrodes and, consequently, minimize the length of the ablation zone. Confirmation that the electrodes are in an appropriate position can be generated by impedance measurements and/or by using any of the standard imaging techniques employed during interventional procedures, such as fluoroscopy or intravascular ultrasound (IVUS), in which transducers are placed on the distal ends of one or both of the longitudinal member. When using tissue impedance measurements, the calcified occlusion body generally exhibits significantly higher impedance than the vessel wall. If an impedance measurement indicates a low impedance value, it is likely that one or both longitudinal members are in contact with the vessel wall, and appropriate repositioning may be warranted. Alternatively, the first and/or the second longitudinal member may be advanced through the subintimal space SIS and then entered into the occlusion body OB in an antegrade fashion.

At step 1020, once the user has confirmed that the first and the second longitudinal members 910 and 920 are positioned at the desired location, one or both of the distal ends 911 and 921 may be redirected such that the electrodes disposed on the first and the second distal ends are positioned towards each other. Furthermore, it is desirable that the electrodes are in contact with the occlusion body OB but are not in contact with the vessel wall to prevent or minimize damage to the vessel wall. At step 1030, the RF treatment may be initiated.

Alternatively, the first and/or the second longitudinal members may be delivered into the occlusion body OB wherein the distal ends are pre-shaped such that redirection of one or more of the distal ends is reduced or not required in order for the distal ends to be substantially positioned towards each other. Additionally, the first and/or the second longitudinal members may be delivered into the occlusion body OB using one or more delivery elements as described above and illustrated in FIGS. 9A-9B.

At step 1040 once a channel has been created, one of the longitudinal members may be withdrawn and the other longitudinal member may be advanced through the occlusion body OB and standard interventional procedures as described above may be performed.

Figure 12:
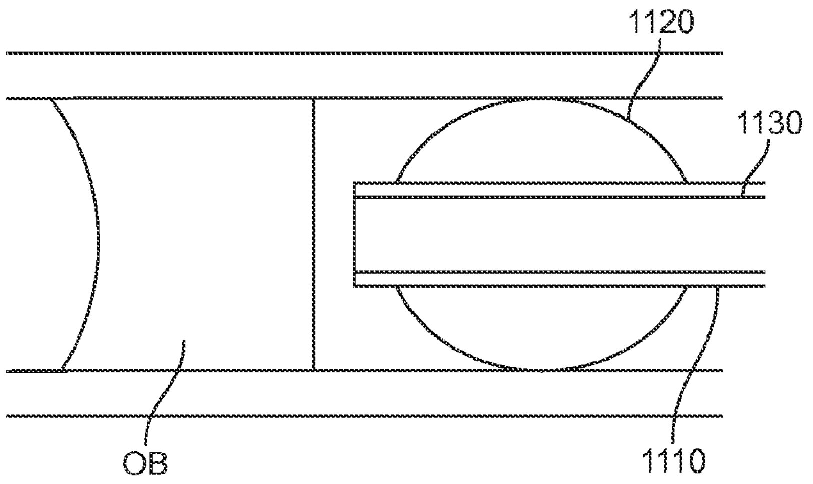
FIG. 12 shows one embodiment of the centering balloon catheter system.

The present embodiments further contemplate a centering balloon catheter system configured to position one or more longitudinal members within the body vessel and reduce the likelihood of the longitudinal members slipping away from a portion of the occlusion. In one embodiment as seen in FIG. 12 the balloon catheter system comprises an inflatable balloon 1120 disposed on a balloon catheter 1110, wherein the balloon may be inflated with a biocompatible fluid such as a gas (CO2) or a liquid such as saline or contrast agents. The inflation medium may be delivered through a separate inflation lumen (not shown). In one embodiment, upon inflation, the balloon 1120 may be configured to occupy substantially the entire interior of a vessel such that the balloon catheter system may be substantially fixed in place within a body vessel.

Optionally, the balloon catheter system may comprise a delivery catheter 1130 disposed within the balloon catheter 1110. The delivery catheter 1130 may be configured to deliver one or more longitudinal members to the occlusion body OB.

Figure 13A:
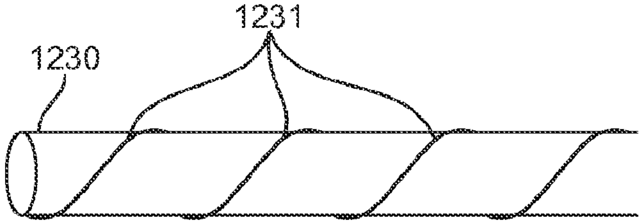
FIG. 13A-13B show one embodiment of the centering balloon catheter system comprising helical groves.
Figure 13B:
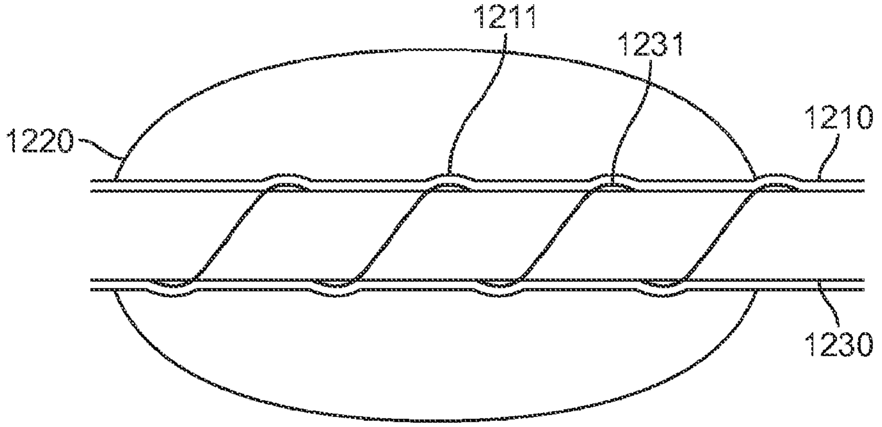

In one embodiment as seen in FIGS. 13A-13B, the delivery catheter 1230 may comprise helical protrusion 1231 and the balloon catheter 1210 comprising an inflatable balloon 1220 may comprise receiving grooves 1211 configured to receive the helical protrusion 1231 disposed on the delivery catheter 1230. The receiving grooves 1211 are configured to allow the helical protrusion 1231 to rotate within the balloon catheter 1210 without moving the balloon catheter 1210. In such configuration, the delivery catheter 1230 may be advanced within the balloon catheter 1210 by twisting or otherwise turning the delivery catheter 1230 while the balloon catheter 1210 maintains a substantially fixed position within the body vessel.

The delivery catheter may comprise a single lumen as seen or it may comprise multiple lumens (not shown). The multi-lumen configuration may be advantageous by facilitating insertion and/or removal of various apparatus during the operation. Furthermore, the multi-lumen configuration may be advantageous such that one or more of the lumens may be configured as suction lumens, wherein suction force may be applied through the suction lumens to stabilize the delivery catheter upon the occlusion body OB as described in co-pending U.S. application Ser. No. 13/042,411 by the same inventors, which is incorporated herein in its entirety.

In a multi-lumen configuration, the lumens may assume various positional configurations relative to another lumen within the catheter. For example, the delivery catheter may comprise two or more lumens configured in a non-coaxial manner. In another embodiment, the delivery catheter may comprise two or more lumens configured in a coaxial manner. It is further contemplated that the lumens may assume various shape and position configurations within the catheter.

Further, in an embodiment where energy may be delivered through the longitudinal members it would be advantageous to have a heat resistant tip on the distal end of the balloon catheter and/or the delivery catheter.

Figure 14:
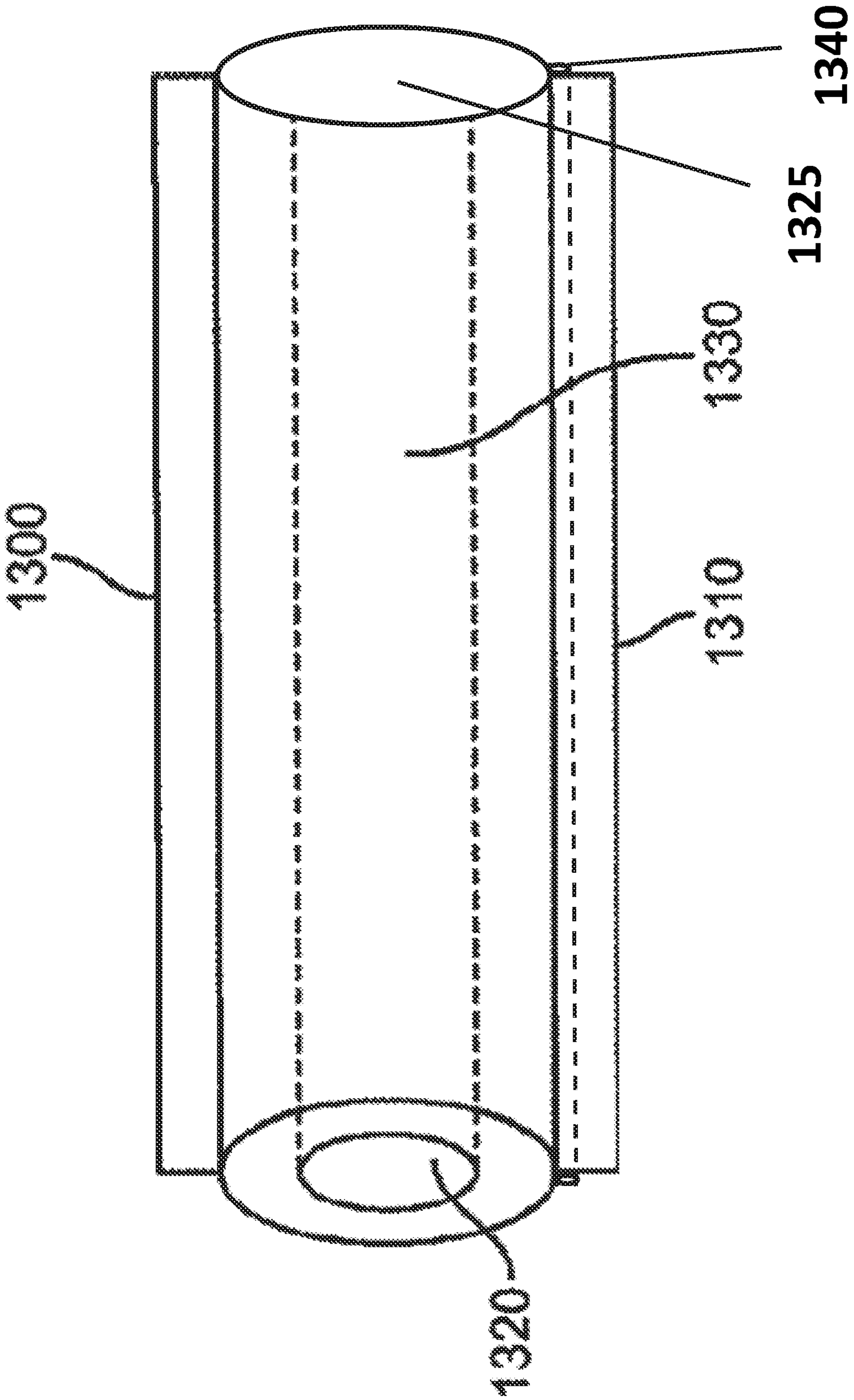
FIG. 14 shows one embodiment of longitudinal member comprising an lumen.

Various embodiments of the longitudinal member described above may further comprise one or more lumens disposed within the interior of the longitudinal member. In one embodiment, as seen in FIG. 14 a longitudinal member with a lumen 1300 comprises a distal opening 1320, a proximal opening (not shown), and an elongated body 1330 disposed in-between. The longitudinal member may be coated with an insulator 1310, such as Teflon, ceramic, polyimide, parylene, or other suitable materials. Examples of methods which could be employed for coating may include spraying, dipping, vapor deposition, or plasma deposition. The proximal opening may be connected to a fluid source and the distal opening 1320 of the lumen is configured to deliver at least one fluid to the treatment region of the blood vessel, wherein the fluid may be transmitted from the fluid source through the elongated body lumen 1330. Alternatively, the longitudinal member may comprise an injection port (not shown) that traverses the coating 1310 to connect a fluid source with the elongated body 1330. The elongated body 1330 may be coated with materials, such as hydrophobic materials that are configured to prevent fluids from exiting the elongated body. It is contemplated that the treatment fluid may be liquids and/or gases such as saline, compressed air, various drugs, or the like.

In one embodiment, the fluid delivered to the treatment region of the blood vessel may be used as coolants to control the temperature of the treatment region during the ablation procedure. Additionally and optionally, the fluid delivered to the treatment region may be used to weaken and/or break up a portion of the occlusion. For example, it is envisioned that compressed air may be delivered into the occlusion during the advancement of the longitudinal member. The compressed gas may be used to enlarge or expand a space in the occlusion already created by the penetration of the occlusion and/or by the ablation. The expanded space created by the compressed air may aid in further advancement of the longitudinal member. Alternatively, it is contemplated that the fluid delivered to the treatment region may serve other functions such as delivering therapeutic agents to the treatment regions and the like.

Furthermore, the fluid delivered to the treatment site through the longitudinal member may be a conductive fluid such as isotonic saline. The fluid may immerse a portion of the target site such that the active electrode disposed on another longitudinal member may generate a current density that is sufficiently high to cause sparks crossing over to the fluid immersed target site. In such an embodiment, the fluid may acts as an energy sink, receiving the energy delivered from the active electrode. It is envisioned that the energy as applied from the active electrode may be sufficient to vaporize the fluid such that plasma may be formed to cause disintegration or breakdown of the occlusion in contact with the plasma.

It is envisioned that various fluids may be delivered in sequence or in tandem. In one embodiment, the guidewire may be advanced at least partly into the occlusion; thereafter, a first fluid, such as compressed air may be delivered into the occlusion to create or expand a space. Thereafter, a second fluid, such as isotonic saline may be delivered into the space created by the first fluid. As described above, the isotonic saline may serve as a conductive fluid that receives radiofrequency energy as delivered by an active electrode. The saline may then be vaporized by the radiofrequency energy to create plasma that causes disintegration of a portion of the occlusion that is in contact with the plasma.

While the above embodiments refer to the use of RF energy for the purpose of ablation, it should be noted that other energy modalities may be used as well, for example ultrasound energy. In one embodiment, one or more longitudinal members of the recanalization systems of the present invention comprise one or more ultrasound transducers, instead of or in addition to RF electrodes. The ultrasound transducers provide ultrasound energy for ablating an occlusion. In one embodiment, the antegrade and/or the retrograde longitudinal members may comprise ultrasound transducers and ablate the lesion from an antegrade as well as a retrograde direction. Other energy modalities could include microwave and laser.

It should be noted that the combined antegrade and retrograde energy delivery techniques described above could also be used as an adjunct technique to crossing CTOs in combination with using conventional methods. The technique could be used to sufficiently soften or weaken the occlusion, thereby allowing a guidewire or catheter to cross the occlusion.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A catheter comprising:

a longitudinal member including:

a helical wire, wherein the wire is configured to dilate a vessel as the catheter is advanced through the vessel while being twisted or rotated;

a tubular liner; and a plurality of wires wound around an outer surface of the tubular liner, wherein the plurality of wires includes a first wire and a second wire, and a cross-sectional diameter of the first wire is different from a cross-sectional diameter of the second wire.

2. The catheter according to claim 1, wherein the longitudinal member further includes a polymer layer formed around the plurality of wires.

3. The catheter according to claim 1, wherein the longitudinal member further includes a hydrophilic coating on an outer surface of the longitudinal member.

4. The catheter according to claim 1, wherein the longitudinal member includes an inner lumen that is configured to receive a guidewire and/or deliver fluid.

5. The catheter according to claim 1, wherein a distal end portion of the longitudinal member includes a marker, and the longitudinal member terminates at the marker.

6. A catheter comprising:

a longitudinal member including:

a tubular liner; and a plurality of wires wound around an outer surface of the tubular liner, wherein the plurality of wires includes a first wire and a second wire, and a cross-sectional diameter of the first wire is different from a cross-sectional diameter of the second wire; and a helical exterior provided on an outer surface of the longitudinal member.

7. The catheter according to claim 6, wherein the helical exterior is configured to dilate a vessel as the catheter is advanced through the vessel while being twisted or rotated.

8. The catheter according to claim 6, wherein the longitudinal member has a tapered distal end portion such that an outer diameter of the distal end portion decreases towards a distal end thereof.

9. The catheter according to claim 6, wherein the longitudinal member further includes a polymer layer formed around the plurality of wires.

10. The catheter according to claim 6, wherein the longitudinal member further includes a hydrophilic coating on the outer surface thereof.

11. The catheter according to claim 6, wherein the longitudinal member further includes a marker at a distal end thereof, and the helical exterior is proximal of the marker.

* * * * *